(12) United States Patent
Allmendinger

(10) Patent No.: US 7,089,811 B2
(45) Date of Patent: Aug. 15, 2006

(54) SYSTEM, APPARATUS, AND METHOD FOR GUIDING AN EXHAUST GAS

(75) Inventor: Klaus K. Allmendinger, San Juan Capistrano, CA (US)

(73) Assignee: Innovate! Technology, Inc., Irvine, CA (US)

( * ) Notice: Subject to any disclaimer, the term of this patent is extended or adjusted under 35 U.S.C. 154(b) by 63 days.

(21) Appl. No.: 10/977,307

(22) Filed: Oct. 29, 2004

(65) Prior Publication Data

US 2005/0160840 A1 Jul. 28, 2005

Related U.S. Application Data

(60) Provisional application No. 60/539,878, filed on Jan. 28, 2004.

(51) Int. Cl.
*G01N 1/20* (2006.01)
*G01N 33/00* (2006.01)

(52) U.S. Cl. .............................. 73/863.51; 73/864.33; 73/23.31

(58) Field of Classification Search ............. 73/23.31, 73/31.05, 863.51, 864.33, 866.5
See application file for complete search history.

(56) References Cited

U.S. PATENT DOCUMENTS

| | | | | |
|---|---|---|---|---|
| 3,803,921 A | * | 4/1974 | Dieterich | 73/203 |
| 4,534,213 A | * | 8/1985 | Mirikidani | 73/118.1 |
| 5,625,156 A | * | 4/1997 | Serrels et al. | 73/863.51 |
| 5,834,657 A | * | 11/1998 | Clawson et al. | 73/863.81 |
| 6,432,288 B1 | * | 8/2002 | Nielsen et al. | 204/424 |
| 6,843,105 B1 | * | 1/2005 | France | 73/31.05 |

* cited by examiner

*Primary Examiner*—Daniel S. Larkin
(74) *Attorney, Agent, or Firm*—Gavrilovich, Dodd & Lindsey, LLP

(57) ABSTRACT

An exhaust guide guides exhaust gases within an exhaust system to an intake portion of a sensor when an input port and an output port of the exhaust guide are positioned within an exhaust gas flow. A high pressure region formed at the input port and a low pressure region formed at the output port facilitate the flow of the gases through a chamber housing that at least houses the intake portion of the sensor. Contamination of the sampled gases by outside air is minimized. In some configurations, the sensor is mounted outside of the exhaust system to increase the thermal isolation between the sensor and the exhaust system improving the performance and increasing the useful life of the sensor.

25 Claims, 10 Drawing Sheets

# US 7,089,811 B2

SYSTEM, APPARATUS, AND METHOD FOR GUIDING AN EXHAUST GAS

RELATED APPLICATIONS

The application claims the benefit of priority of U.S. Provisional Patent Application Ser. No. 60/539,878, entitled "SYSTEM, APPARATUS, AND METHOD FOR GUIDING AN EXHAUST GAS", filed Jan. 28, 2004 and which is incorporated by reference in its entirety herein.

BACKGROUND OF THE INVENTION

The invention relates in general to exhaust guides and more specifically to an apparatus, system and method for guiding an exhaust gas to measure an oxygen concentration.

Oxygen sensors are used to measure the concentration of oxygen in a gas. Many conventional combustion engines utilize oxygen sensors for determining the air to fuel mixture of the exhaust of the combustion engine. Conventional internal combustion engines typically incorporate electronic fueling control using computing devices such as Electronic Control Units (ECU) that meter fuel into the engine intake depending on engine intake airflow. The oxygen sensors are typically mounted within the exhaust system along the engine exhaust gas flow. The exhaust gases flow through an intake of the exhaust sensor exposing a measuring cell within the oxygen sensor to the exhaust gases. The oxygen sensor produces an output signal that indicates the air to fuel ratio of the exhaust gas.

Conventional techniques for measuring exhaust gases, however, are limited in several ways. The exhaust flow within the exhaust system oscillates at least in magnitude and, in some circumstances, also in direction. External air is often sucked back into the exhaust system through the tail pipe. When the oxygen sensor is mounted near the exhaust output, the exhaust gases that are measured are often contaminated by external air which results in an inaccurate oxygen concentration measurement. One attempted solution to this problem includes placing the oxygen sensor or an exhaust guide in the exhaust system away from the exhaust output. If the sensor is permanently mounted within the exhaust system, conventional techniques include modifying a portion of the exhaust system to include a mounting apparatus for the sensor. A typical technique includes cutting an opening within a exhaust pipe and welding a bung within the opening. An oxygen sensor is then screwed into the threaded bung. A significant drawback of this technique includes the extra cost and inconvenience resulting from the exhaust system modification. In addition, the exhaust gases near the engine are often much hotter than near the output. Oxygen sensors mounted near the engine experience high temperatures and well as large temperature variations resulting in deterioration and premature failure of the oxygen sensor. Where the measurement is a performed infrequently, and the presence of the oxygen sensor is temporary, a typical measuring technique includes inserting a long exhaust guide such as pipe into the output of the exhaust system. The long pipe provides the oxygen sensor with exhaust gases that are sampled at a distance form the exhaust opening where contamination from external air is less likely. This technique is limited in that significant measurement delays result from the time required for the sampled gases to travel along the pipe. Changes in oxygen concentration resulting from adjustments and changing engine conditions can not be easily correlated due to the measurement delays.

Therefore, there exists a need for an apparatus, system and method for guiding a gas to a sensing portion of a sensor.

DETAILED DESCRIPTION OF THE PREFERRED EMBODIMENTS

In an exemplary embodiment of the invention, an exhaust guide directs exhaust gases past a measuring portion of a sensor when an input port and an output port of the exhaust guide are positioned within an exhaust flow. The input port and output port are connected to a chamber housing and configured to receive exhaust gases through the input port, direct the exhaust gases through a chamber within the chamber housing, and expel the exhaust gases from the output port allowing the sensor positioned within the chamber to sample the exhaust gases. The configuration and orientation of the input port and output port result in the creation of a high pressure region near an input aperture of the input port and a low pressure region near an output aperture of the output port when the exhaust guide is properly orientated within the exhaust flow. In the exemplary embodiment, the low pressure region is created during both positive and negative flow cycles resulting in a nearly continual low pressure region near the output port.

Figure 1:
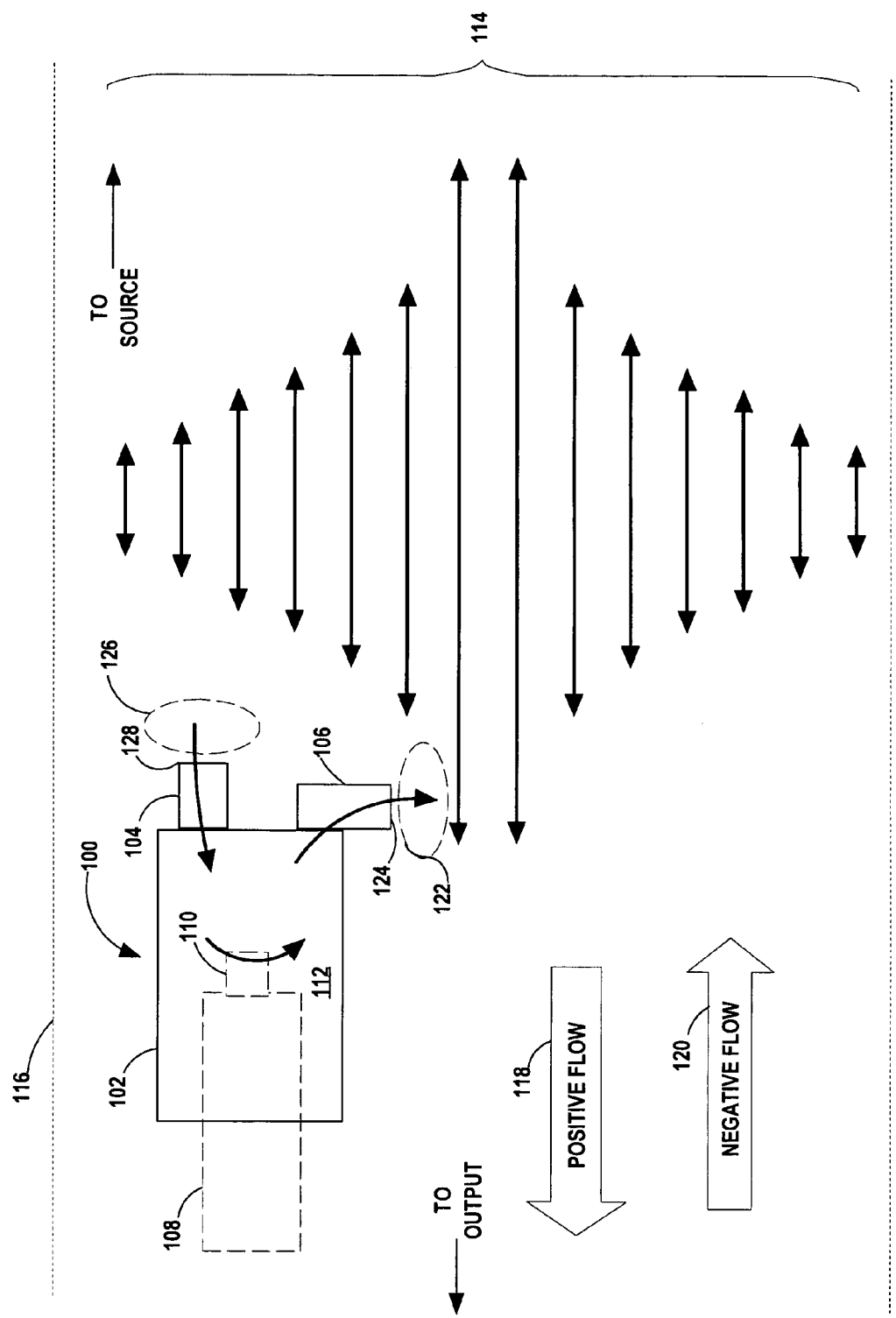
FIG. 1 is a block diagram of an exhaust guide within an exhaust system in accordance with an exemplary embodiment of the invention.

FIG. 1 is a block diagram of a side view of a gas guide 100 within a gas channel 116 in accordance with an exemplary embodiment of the invention. FIG. 1 includes various blocks that represent components, regions, and areas within the gas guide 100 in an illustrated arrangement that parallels a schematic representation of sectional side views of gas guides in accordance with the exemplary embodiments. The blocks illustrated in FIG. 1 do not necessarily represent the relative sizes or positions of the components or regions of the gas guide 100. As discussed below in further detail, the gas guide 100 may be formed as an integrated unit from a single material or may be implemented using two or more components of similar or different materials. The various functions and operations of the functional blocks described with reference to FIG. 1 may be implemented using any number of components or elements. The gas guide 100 may be used to guide any gas or other fluid past a sensing device when the gas guide 100 is positioned within a gas or fluid flow. Accordingly, the principles and techniques discussed herein may be applied in a variety of circumstances in any of numerous industries without departing from the scope of the invention. The exemplary embodiments presented below are discussed with reference to uses of measuring oxygen concentration of exhaust gases within an exhaust system connected to a combustion engine. Those skilled in the art will readily apply the teachings herein in accordance with known techniques to other implementations, industries, and applications.

The gas guide 100 includes at least a chamber housing 102, an input port 104 and an output port 106. The chamber housing 102 is configured to receive and hold a sensor 108 in a manner such that at least the intake portion 110 of the sensor 108 is positioned within the chamber 112 of the chamber housing 102. The intake portion 110 of the sensor 108 typically includes several openings that allow the gases to be sampled to enter the sensor 108. The sensor 108 is drawn using dashed lines in FIG. 1 to illustrate that the sensor 108 is not part of the gas guide 100 in the exemplary embodiment. In some circumstances, however, the sensor 108 may be permanently secured to the gas guide 100. For example, the sensor 108 may be implemented to include the gas guide 100 in an integrated device in some situations. As explained below in further detail, the sensor 108 is screwed into a threaded bore (not shown) of the chamber housing 102 in the exemplary embodiments. Other moutiung techniques can be used in some circumstances.

During operation, the gas guide 100 is mounted in the gas flow 114 within a gas channel 116 such as an exhaust system (116) connected to a combustion engine. The gas guide 100 includes the appropriate configuration and mounting mechanisms to secure the gas guide 100 at the desired location within the gas channel (exhaust system) 116. The gas guide 100 is illustrated as being completely contained within the gas channel 116. In some circumstances, at least a portion of the gas guide 100 may be located outside of the gas channel 116. For example, the oxygen sensor 108 may be positioned completely outside of the exhaust system (116) as described below with reference to second, third, and fourth exemplary embodiments of the invention. Where the gas channel 116 is an exhaust system (116), the exhaust gas flow 114 within the exhaust system 116 generally flows from its source at the exhaust valve of the engine toward an exhaust output1 such as a tail pipe. The gas flow direction (118,120), however, may oscillate between a positive flow 118 from the exhaust valve toward the output and a negative flow 120 from the output toward the engine. Accordingly, the lines representing the gas flow 114 in FIG. 1 are drawn with arrow heads on both ends to illustrate that the gas flow 114 may flow in both directions. The frequency of the oscillation depends on the number of engine cylinders and the engine speed as well as other factors. The oscillations are more pronounced during slow engine speeds and with engines having fewer cylinders. The lengths of the arrows denoting the gas flow 114 in FIG. 1 represent the relative pressure and velocity of the gas flow 114 across the diameter of the exhaust system gas channel 116. In accordance with well known fluid dynamics principles, the speed of the gas flow 114 near the center of the channel 116 is greater than the speed near the inner surface of the channel 116. The general direction of positive gas flow is illustrated with arrow 118 and the negative gas flow direction is illustrated by arrow 120 in FIG. 1.

The output port 106 is configured to pull gases from the chamber 112 when the gases flow past the output port 106. When the gas flow 114 moves past the output port 106, a low pressure region 122 is formed at the output aperture 124 of the output port 106. The shape of the output port 106 and the orientation of the output aperture 124 relative to the direction of the gas flow 114 are configured to result in a gas flow 114 near the output aperture 124 that creates the low pressure region 122. As discussed below, the output port 106 is configured to include an output conduit that positions the plane of the output aperture 124 at an angle to the gas flow 114 to create the low pressure region 122 in the exemplary embodiment. Operation of the output port 106 can be explained with reference to the Bernoulli's Principle and the "venturi effect". As observed in the exemplary embodiment, Bernoulli's principle can be generally summarized as the theory that an increase in the speed of a flowing fluid results in a decrease in pressure. Accordingly, when the gas is forced to travel around a longer path near the output port 106, its speed must increase and, as a result, a low pressure region 122 in the exhaust flow 114 is formed at the output port 106. The output port 106, therefore, forms a "venturi" where the higher pressure gases inside the chamber 112 try to equalize the lower pressure at the output port 106 and are, therefore, sucked toward the output aperture 124. Examples of other suitable output port 106 configurations include baffles or flaps strategically aligned to create the low pressure region 122.

The input port 104 is configured to create a high pressure region 126 at the input aperture 128. As the angle of the plane of the aperture to the gas flow direction approaches 90 degrees, the pressure at the input aperture 128 increases. By positioning the input aperture 128 laterally toward the gas flow 114 direction, the high pressure region 126 is formed at the input aperture 128. The combination of the high pressure region 126 and the low pressure region 122 create an efficient flow of gases from the input port 104, through the chamber 112, and out through the output port 106.

Figure 2:
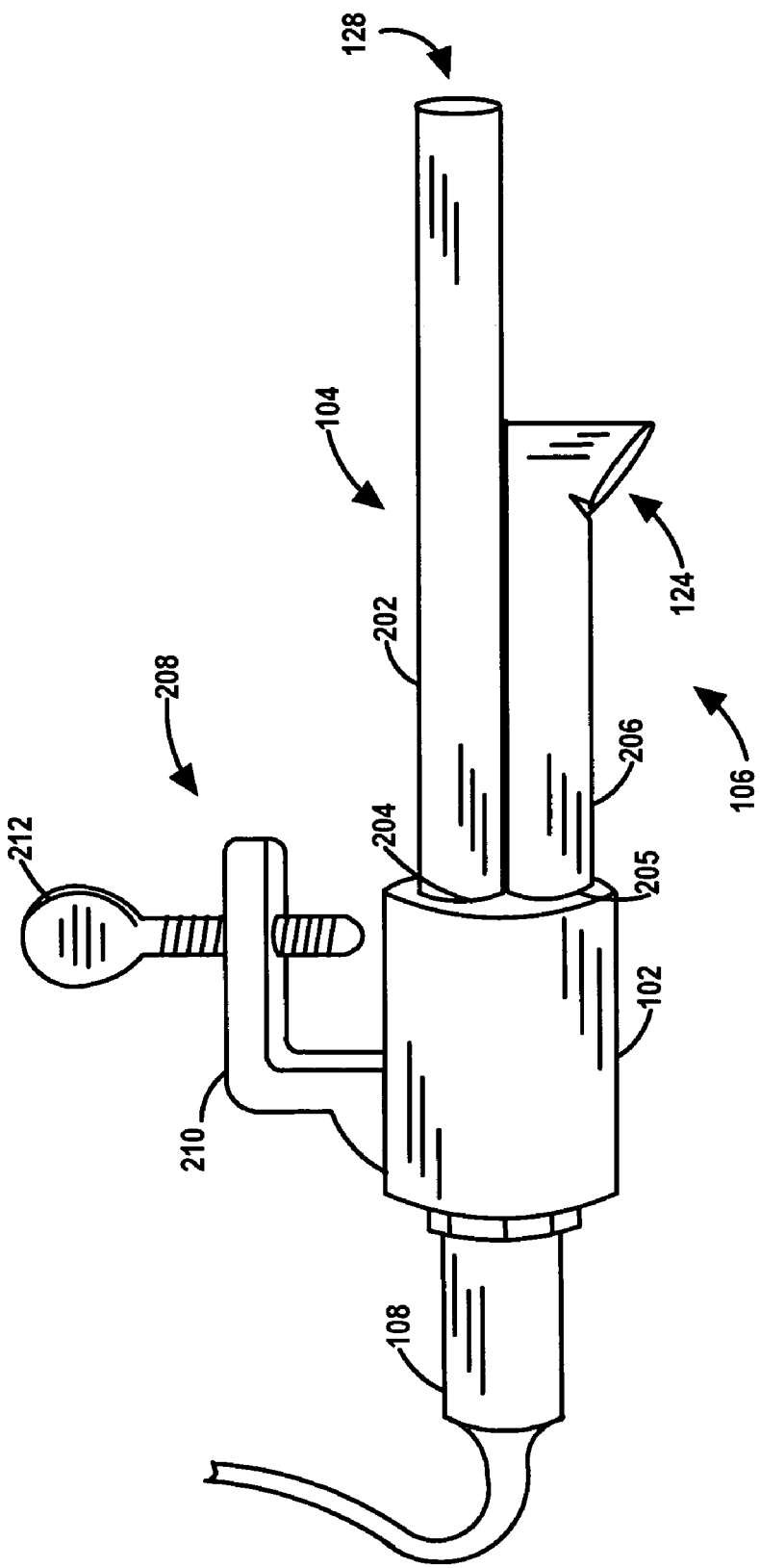
FIG. 2 is an illustration of a perspective view of an exemplary exhaust guide suitable for mounting near the output of an exhaust system.

FIG. 2 is an illustration of a perspective view of an exemplary exhaust guide 200 suitable for mounting near the output of an exhaust system 116. The exhaust guide 200 may be implemented using a variety of materials and configurations. The exhaust guide 200 may be formed form any combination of solid metals, alloys, and ceramics that can withstand the temperature changes in the particular environment without significant deformation or deterioration. Examples of suitable materials include stainless steel, copper and cast aluminum.

In the exemplary embodiment, the input port 104 includes an input conduit 202 having an input aperture 128 opposite a chamber end 204 connected to the chamber housing 102. The input aperture 128 is positioned to face the exhaust gas flow 114 in the exemplary embodiments. The output port 106 includes an output conduit 206 having an output aperture 124 opposite a chamber end 205 connected to the housing chamber 102. The plane of the output aperture 124 is aligned laterally to the exhaust flow 114 when the exhaust guide 200 is mounted in an exhaust pipe of the exhaust system 116. The output conduit 206 is configured to align the plane of the output aperture 124 nearly parallel to the exhaust gas flow 114 in the exemplary embodiment. When the exhaust guide 200 is mounted to position the plane of the input aperture 128 at a right angle to the exhaust gas flow 114, therefore, the plane of the output aperture 124 is positioned at a slight angle to the exhaust gas flow 114. As described below in further detail, the output aperture 124 is angled slightly toward the exhaust system output in an exemplary embodiment where the output conduit is a pipe. In other exemplary embodiments, a bevel is formed near the output aperture 124 and the plane of the output aperture 124 is parallel to the exhaust flow.

Although any of several mechanisms and techniques may be used to mount the exhaust guide 200, a mounting mechanism 208 includes a clamp arm 210 and a clamp screw 212 in the first exemplary embodiment. The clamp screw 212 may be a screw, thumb screw, screw knob, or other type of threaded member that can be tightened to secure the exhaust guide 200. The exhaust guide 200 is positioned near the end of an exhaust system 116 such as in the tail pipe by tightening the clamp screw 212 until significant pressure is achieved between the end of the clamp screw 212 and the edge of the tail pipe. In the exemplary embodiment, the input aperture 128 is positioned along an outer portion of the interior of the exhaust tail pipe and the output aperture 124 is positioned near the inner portion of the interior of the exhaust tail pipe. As discussed below in further detail, this configuration further reduces the likelihood of contamination from external air in the chamber 112 during backflow conditions.

Figure 3:
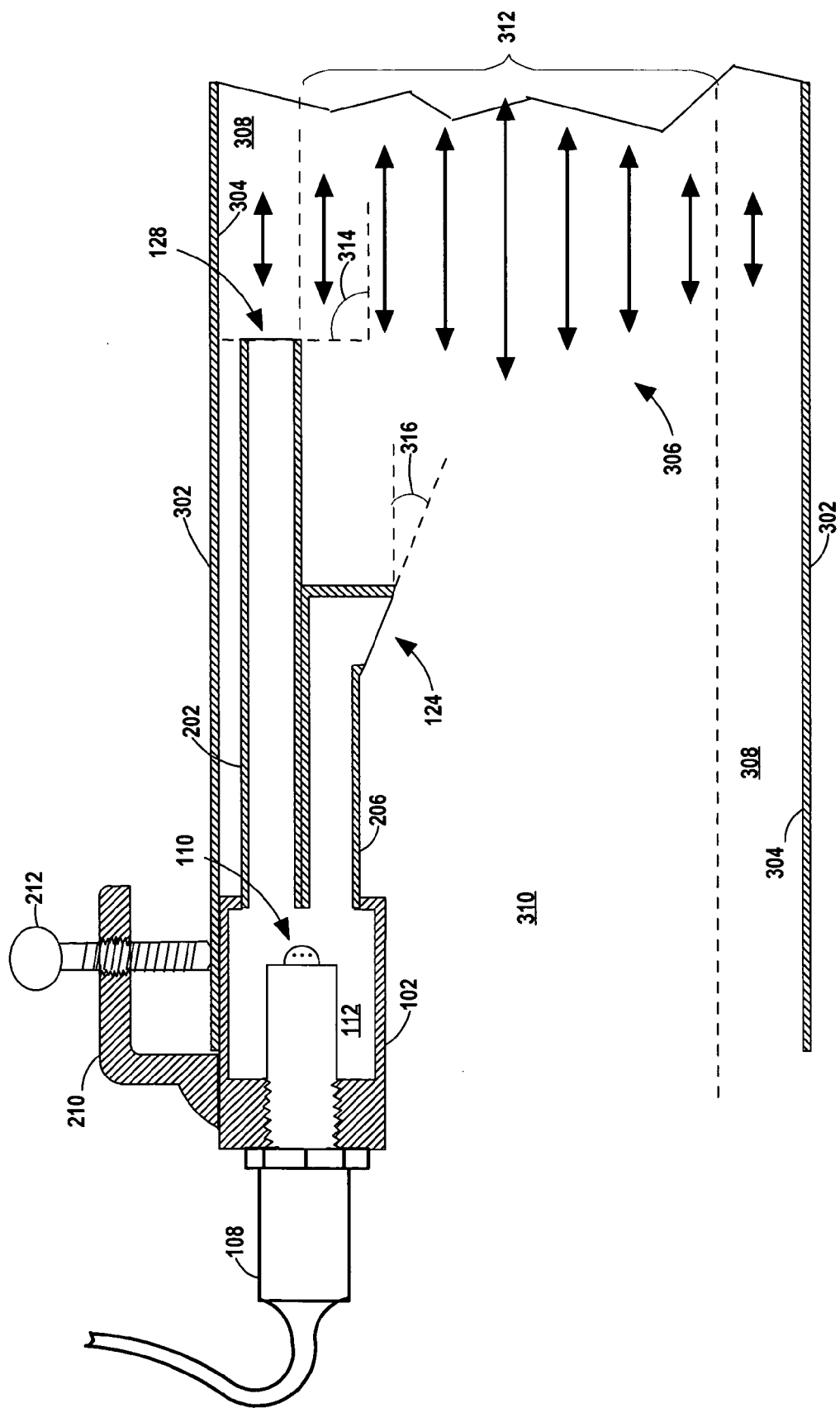
FIG. 3 is an illustration of a sectional side view of an exemplary exhaust guide mounted near an output of an exhaust system.
Figure 4:
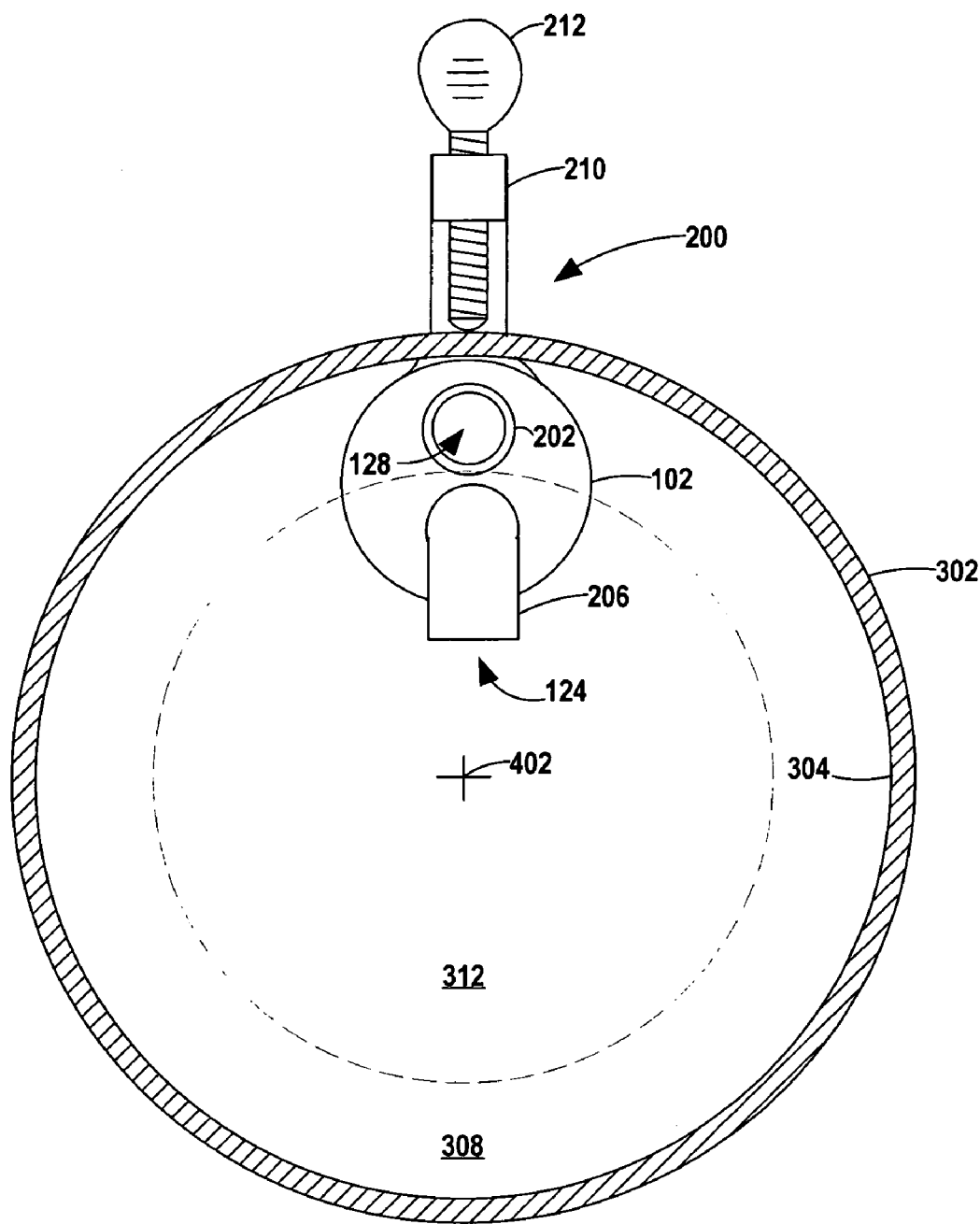
FIG. 4 is an illustration of a front view of an exemplary exhaust guide mounted near the output of the exhaust system.

FIG. 3 is an illustration of a cross sectional side view and FIG. 4 is an illustration of a front view of the exhaust guide 200 mounted in a tail pipe 302 in accordance with the first exemplary embodiment. The input conduit 202 is positioned near the inner surface 304 of the tail pipe 302 placing the input aperture 128 within the outer region 308 of the interior 310 of the exhaust tail pipe 302. As the exhaust gases travel down the exhaust pipe 302, the exhaust gases near the inner region 312 travel at faster rates than the gases near the tail pipe inner surface 304 (within outer region 308). The lengths of the arrows (306) denoting the exhaust flow 306 in FIG. 3 represent the relative pressure and velocity of the exhaust flow 306 across the diameter of the exhaust tail pipe 302. In accordance with well known fluid dynamics principles, the speed of the exhaust flow 306 near the center 402 of the exhaust pipe 302 is greater than the speed near the inner surface 304 of the exhaust pipe 302. By positioning the input conduit 202 farther from the center 402 of the exhaust pipe 302 than the output conduit 206, contamination of the sampled gasses by gases outside of the exhaust system 116 are minimized. During operation of the combustion engine, the exhaust flow 306 follows a time-varying function where the frequency of the oscillations depends on the number of cylinders and the rotational speed of the engine. At low speeds, the direction become negative during a portion of the cycle and air near the output of the tail pipe 302 may be sucked back into the exhaust pipe 302. As the speed of the engine increases, a smaller portion of the cycle is negative. During slower speeds, such as during idle conditions, the outside air is pulled into the exhaust system 302. If allowed to enter the chamber 112, the outside air contaminates the gasses being measured resulting in an inaccurate oxygen concentration measurement. At least two features of the first exemplary exhaust guide 200 minimize contamination of the measured gasses. Since the low pressure region 122 is formed near output port 106 during negative exhaust flow 120 as well as during positive exhaust flow 118, exhaust gasses are nearly continuously flowing through the chamber 112 from the input port 104 to the output port 106. Since the change in direction and pressure is more pronounced in the inner region 312, outside air sucked into the tail pipe 302 flows primarily within the inner region 312. The exhaust gasses in the outer region 308 near the inner surface 304 of the tail pipe 302, therefore, are less likely to be contaminated with external air. As a result, the gasses entering the chamber 112 through the input port 104 are less likely to include external air that has been sucked back into the exhaust system 302 during negative cycles of the exhaust flow 306.

Although the input aperture 128 may have any of several configurations, shapes, and orientations, the input aperture 128 is a circular opening where the plane of the circle defining the opening is perpendicular to the exhaust flow 306 when the exhaust guide 200 is mounted within the tail pipe 302. The angle 314 between the direction of the exhaust flow 306 and the plane of the input aperture is 90 degrees or nearly 90 degrees. The high pressure region 126 is maximized when the plane of the input aperture 128 is perpendicular to the exhaust flow 306.

The angle 316 between the plane of the output aperture 124 and the exhaust flow 114 can be anywhere between zero degrees and thirty degrees. The angle 316 is zero degrees when the output aperture is parallel to the exhaust flow 306 and is 90 degrees where the output aperture 124 is perpendicular to the exhaust flow 306. As the angle 316 between the plane of the output aperture 124 and the exhaust flow approaches 0 degrees from 90 degrees, the low pressure region increases. In most situations, the low pressure region 122 will be at an optimum level when the angle 316 is between 1 and 4 degrees. In the first exemplary embodiments the angle 316 is between 2 and 3 degrees and is approximately 2.5 degrees. Therefore, the bevel angle 316 may greater than 0, 1, or 2 degrees and/or less than 3, 4, or 30 degrees.

Although the tail pipe 302 is a cylinder and has a circular cross section in the exemplary embodiment, the tail pipe 302 may have any of several shapes and configurations. For example, the tail pipe 302 may have a larger cross sectional area than the exhaust pipe connecting the tail pipe 302 to the exhaust manifold. Further, in some circumstances, the tail pipe 302 may have a rectangular cross section.

Figure 5:
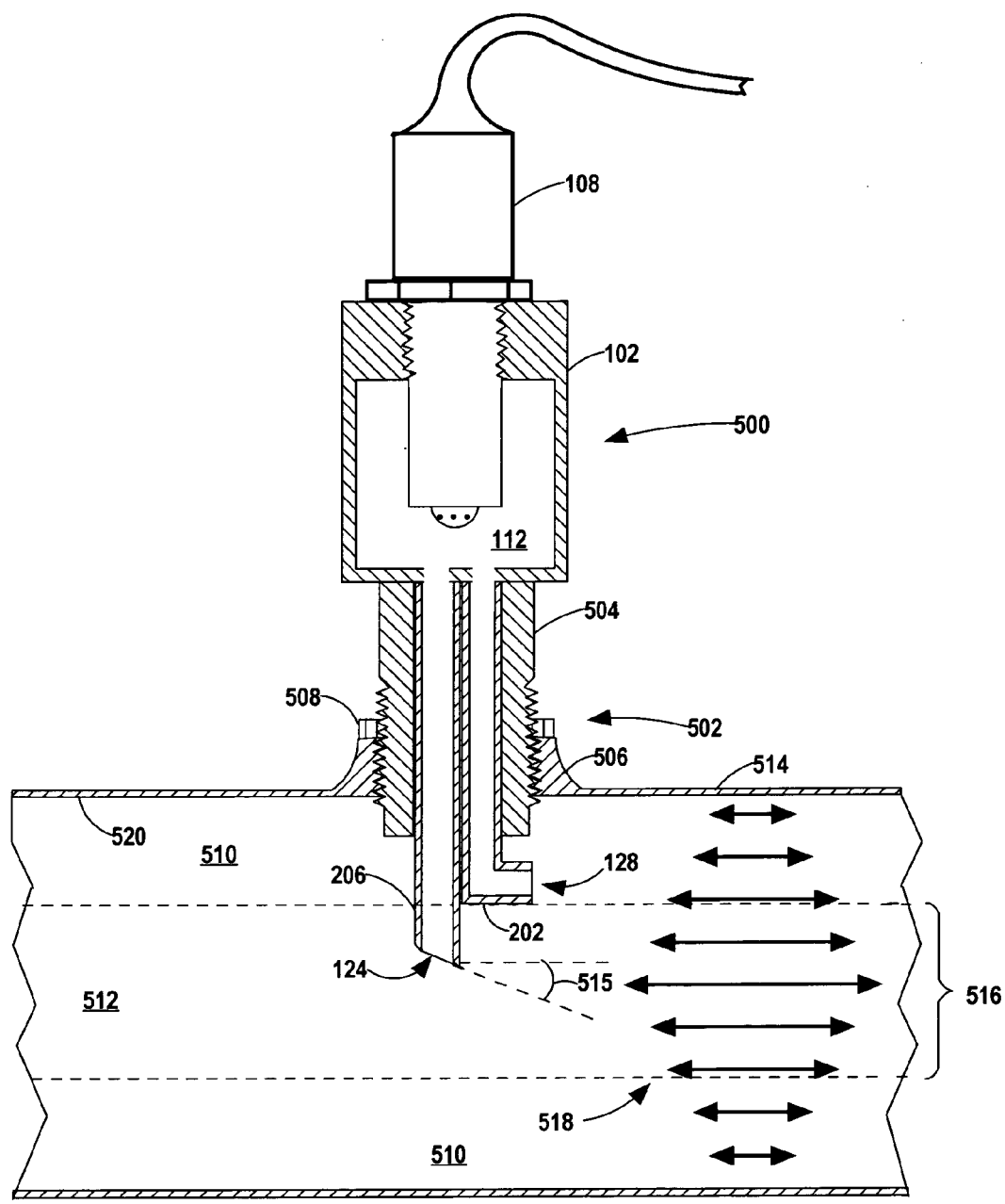
FIG. 5 is an illustration of a sectional side view of an exhaust guide in accordance with a second exemplary embodiment where at least a portion of the sensor is positioned outside of the exhaust channel.
Figure 6:
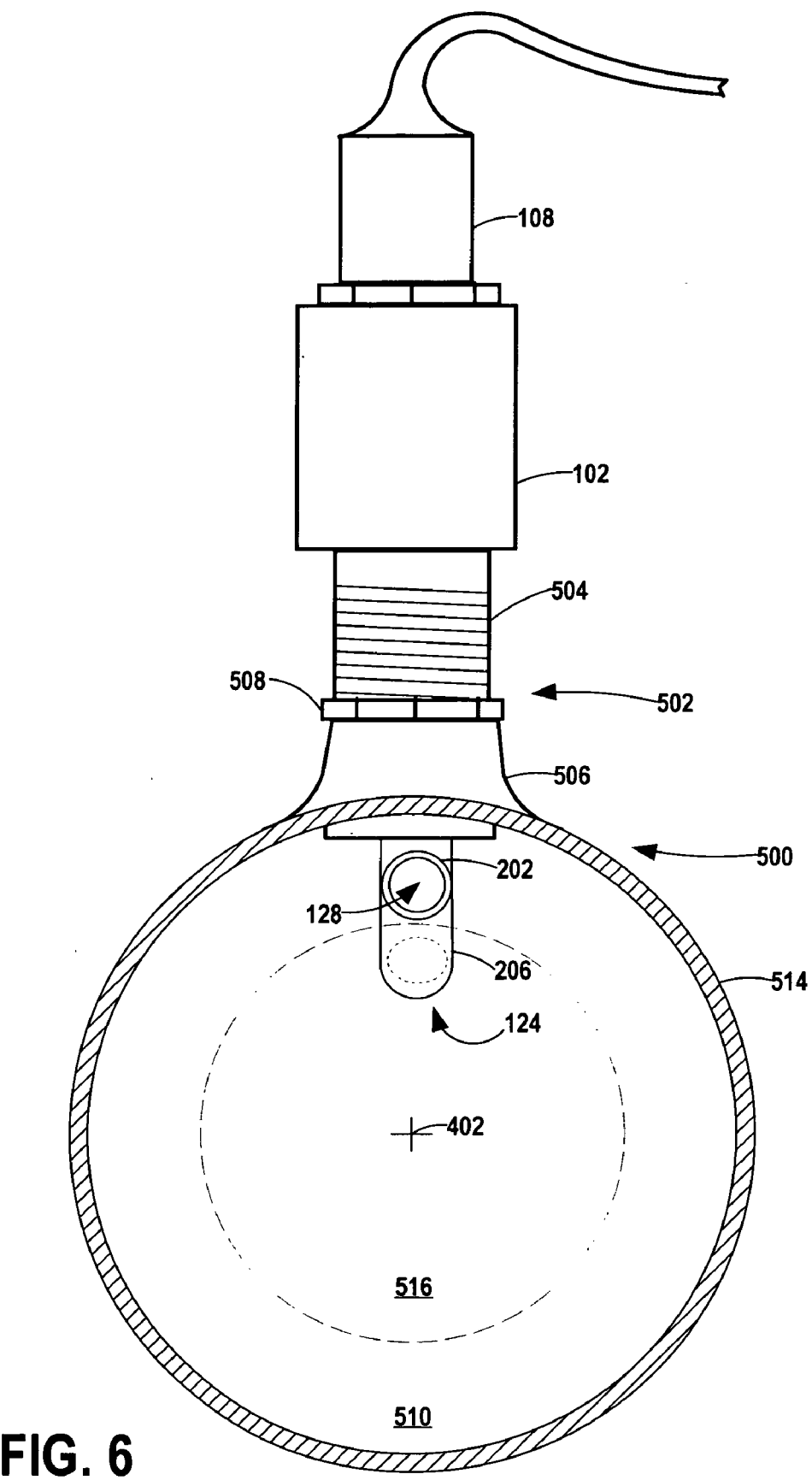
FIG. 6 is an illustration of a front view of the exhaust guide in accordance with a second exemplary embodiment where at least a portion of the sensor is positioned outside of the exhaust channel.

FIG. 5 is an illustration of a sectional side view and FIG. 6 is an illustration of a front view of an exhaust guide 500 in accordance with a second exemplary embodiment where the oxygen sensor 108 is positioned outside of the exhaust system 116. The second exemplary exhaust guide 500 includes a mounting mechanism 502 that positions the oxygen sensor 108 outside the exhaust system 514. Although other mounting mechanisms 502 and techniques may be used in some circumstances, the mounting mechanism 502 in the second exemplary embodiment includes a tube 504 threaded into a bung 506 that is welded into the exhaust system 514. The exhaust guide 500 includes a marking (not shown) indicating the orientation of the input aperture 128 within the exhaust system 514. The marking provides a mechanism for properly aligning the exhaust guide 500 within the exhaust system 514. After the tube 504 is threaded into the bung 506 and positioned at the appropriate depth and orientation, a locking nut 508 secures the exhaust guide 500 to maintain the appropriate position in the second exemplary embodiment. An example of another technique for aligning and securing the exhaust guide 500 includes tightening the exhaust guide 500 into the bung 506 to deform a compression washer (not shown) positioned between the top of the bung 506 and a bottom seat of exhaust guide 500. With such a mounting mechanism, the exhaust guide 500 is tightening until the exhaust guide 500 is secured in the appropriate orientation to the exhaust flow 518. The marking allows the installer to properly align the exhaust guide 500 in the exhaust channel 514.

In the second exemplary embodiment, the input port 104 is an input conduit 202 including an elbow to position the plane of the input aperture 128 perpendicularly to the exhaust flow 518. The output port 106 includes an output conduit 204 206 having an output aperture 124 positioned at an angle 515 of approximately 2 to 3 degrees to the exhaust flow 518 in the exemplary embodiment. The angle 515 may be other values and should be between 0 and 30 degrees in most circumstances. In many situations, a suitable value for the angle 516 is between 1 and 4 degrees. Therefore, the bevel angle 515 may greater than 0, 1,or 2 degrees and/or less than 3, 4, or 30 degrees. The input aperture 128 is positioned within the output region 510 of the interior 512 of the exhaust channel 514 and the output aperture 124 is positioned within the inner region 516 within the interior 512 of the exhaust channel 514. As explained above, positioning the input aperture 128 within the outer region 510 near the interior surface 520 of exhaust channel 514 minimizes contamination by external air where the exhaust guide 500 is mounted near the exhaust output. Where the exhaust guide 500 is mounted near the engine, the positions of the apertures 124,128 are less critical for minimizing contamination.

The exhaust channel 514 may be any portion of the exhaust system and may have any of several shapes and sizes. The exhaust channel 514 is shown as a cylindrical pipe or tube in FIG. 5 and FIG. 6. The second exemplary exhaust guide 500 may be mounted in a section of exhaust pipe, to an exhaust manifold, or anywhere in the exhaust system where exhaust gases are sampled and measured.

As explained above, conventional systems are limited in that the oxygen sensor experiences high temperatures and large temperature variations resulting in premature failure of the oxygen as well as a decrease in the accuracy of the oxygen concentration measurement when the oxygen sensor is mounted near the engine. In the second exemplary embodiment, the temperature of the oxygen sensor 108 is significantly reduced improving performance as well as the useful life of the oxygen sensor 108. By reducing the proximity of the oxygen sensor 108 to the extremely high temperature exhaust gases and exhaust system 116 components, the ambient temperature near the oxygen sensor 108 is greatly reduced. The oxygen sensor 108 is further thermally isolated by insulating the input conduit 202 and the output conduit 206 from the exhaust channel 514. In some circumstances, a material having a high thermal resistance can be used to fill the area between the conduits 202, 206, and the tube 504. Also, materials having a relatively low thermal conduction may be used to form one or more components of the exhaust guide 500.

Figure 7:
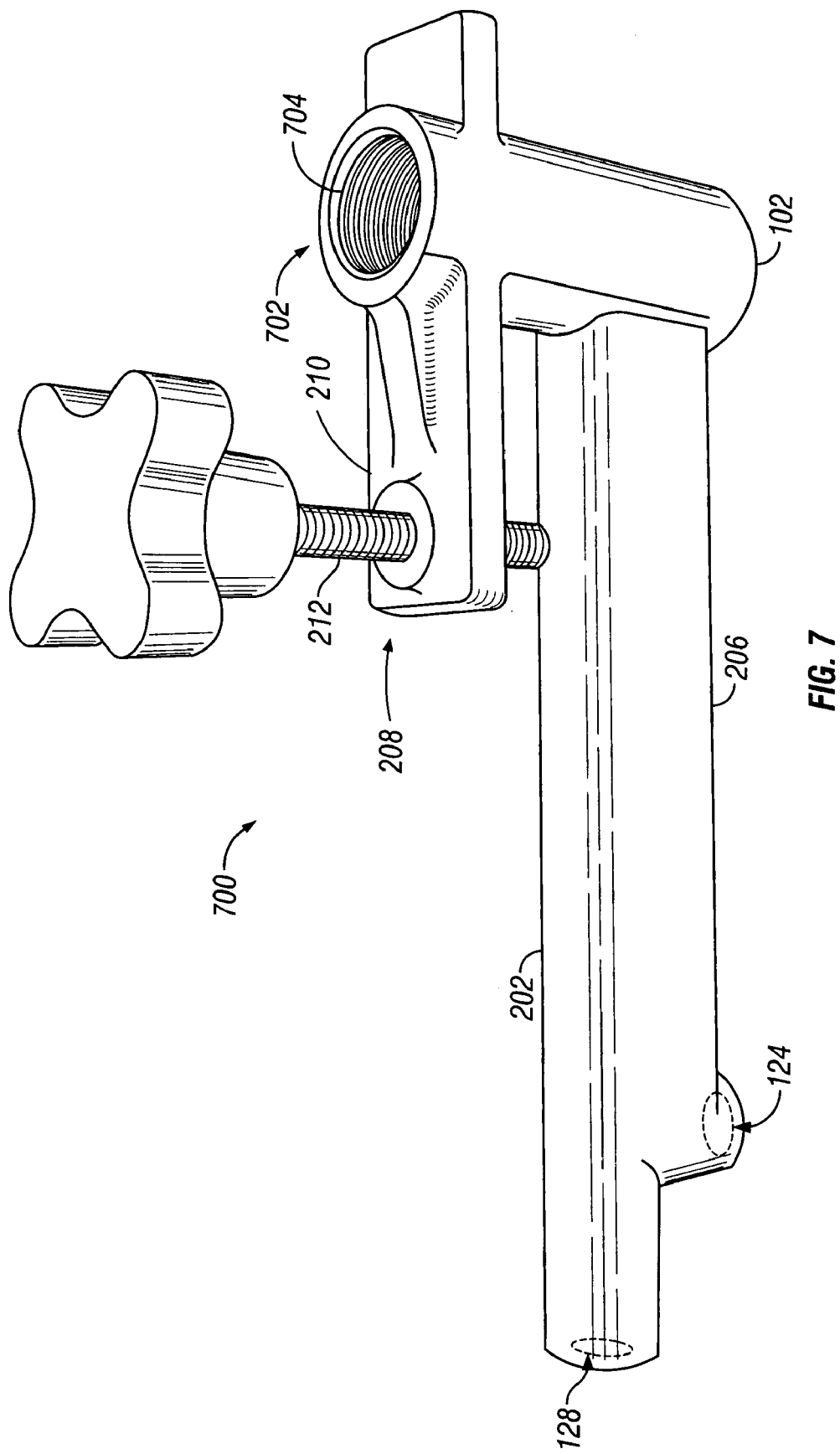
FIG. 7 is an illustration of a perspective view of an exhaust guide in accordance with a third exemplary embodiment of the invention.
Figure 8:
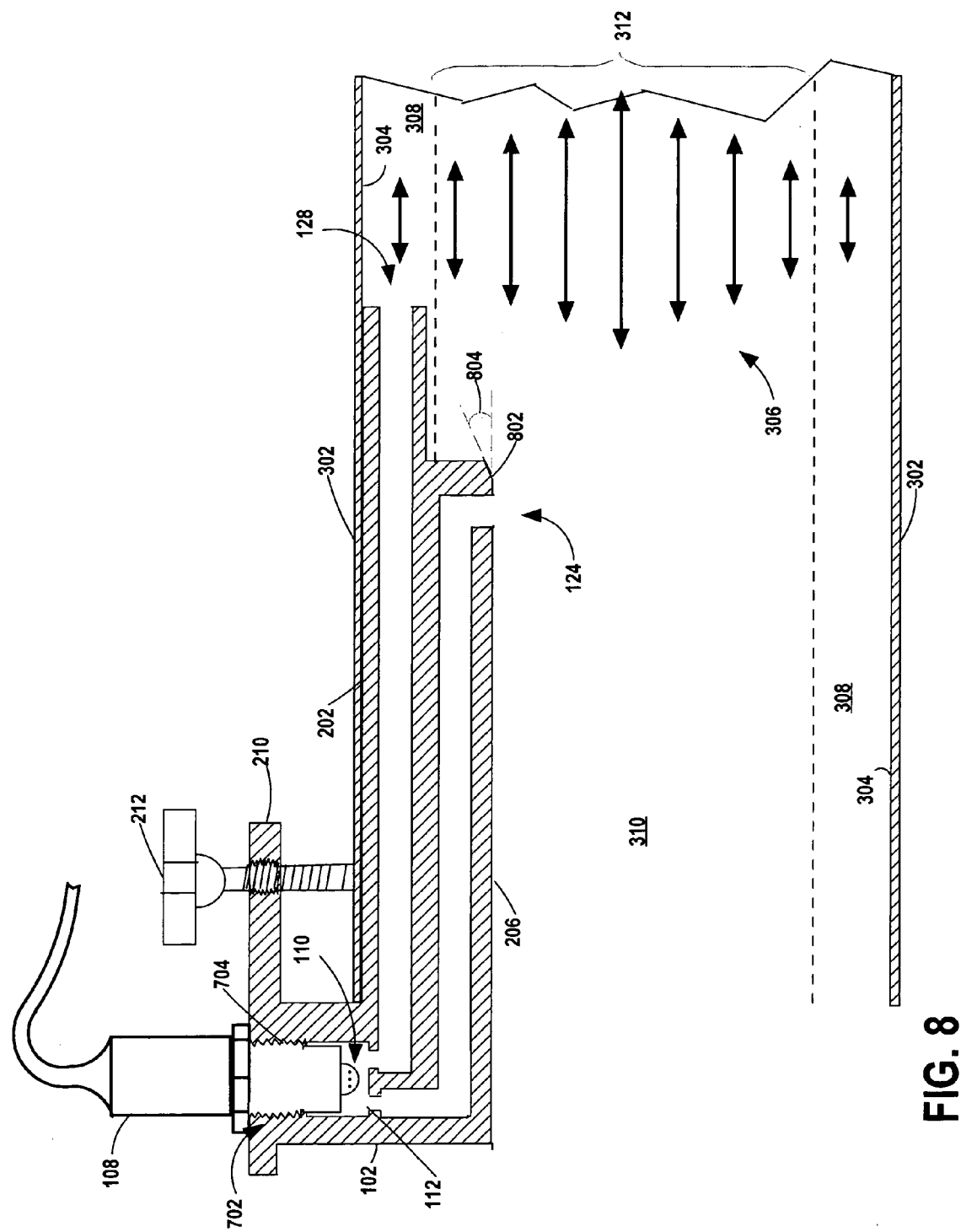
FIG. 8 is an illustration of a cross sectional side view of the exhaust guide in accordance with the third exemplary embodiment of the invention.

FIG. 7 is an illustration of a perspective view and FIG. 8 is an illustration of a cross sectional side view of an exhaust guide 700 in accordance with a third exemplary embodiment of the invention. Although any of several materials can be used to form the exemplary guide 700, the exhaust guide 700 is cast aluminum in the third exemplary embodiment. In accordance with known techniques, the exhaust guide 700 is cast and machined to form a single piece of aluminum that includes at least an input conduit 202 having an input aperture 128, output conduit 206 having an output aperture 124, and a chamber housing 102. In the third exemplary embodiment, therefore, the input port 104, the output port 106, and the chamber 112 are formed from channels and cavities within a single cast aluminum body.

Although the input aperture 128 may have any of several configurations, shapes, and orientations, the input aperture 128 is a circular opening where the plane of the circle defining the opening is perpendicular to the exhaust flow 306 when the exhaust guide 700 is mounted within the tail pipe 302. The angle between the direction of the exhaust flow 306 and the plane of the input aperture is 90 degrees or nearly 90 degrees. The high pressure region 126 is maximized when the plane of the input aperture 128 is perpendicular to the exhaust flow 306.

Although the output aperture 124 may be slightly angled from the direction of the exhaust flow 314, the output conduit 206 includes a bevel 802 in the third exemplary embodiment. The bevel 802 has a configuration such that a bevel angle 804 is formed between the plane of the bevel 802 and the exhaust flow 306 when the exhaust guide 700 is mounted in the tail pipe 302. Although the angle may be in the range from 0 to 30 degrees, examples of suitable values of the bevel angle 804 include values in the range between 1 and 4 degrees. In the third exemplary embodiment, the bevel angle 804 is between 2 and 3 degrees. Therefore, the bevel angle 804 may greater than 0, 1, or 2 degrees and/or less than 3, 4, or 30 degrees.

Although any of several mechanisms and techniques may be used to mount the exhaust guide 700, a mounting mechanism 208 includes a clamp arm 210 and a clamp screw 212 in the third exemplary embodiment. The clamp screw 212 may be a screw, thumb screw knob, or other type of threaded member that can be tightened to secure the exhaust guide 700. The exhaust guide 700 is positioned near the end of an exhaust system 116, such as in the tail pipe 302, by tightening the clamp screw 212 until significant pressure is achieved between the end of the clamp screw 212 and the outer edge of the tail pipe 302. In the exemplary embodiment, the input aperture 128 is positioned along an outer portion of the interior 304 of the exhaust tail pipe and the output aperture 124 is positioned near the inner portion of the interior of the exhaust tail pipe 302. As discussed below in further detail, this configuration further reduces the likelihood of contamination from external air in the chamber 112 during backflow conditions.

The exhaust guide 700 includes a threaded opening 702 to receive the oxygen sensor 108. Threads 704 are machined into the opening 702 after the body of the exhaust guide 700 is cast. In the third exemplary embodiment, the oxygen sensor 108 is positioned outside of the exhaust flow 306 when the exhaust guide 700 is secured to the tail pipe 302. Positioning the oxygen sensor 108 outside of the exhaust flow 306 reduces the operating temperature of the oxygen sensor 108 in most situations. Since the oxygen sensor 108 is not directly exposed to the hot exhaust gases, the oxygen sensor 108 remains cooler. Further, the oxygen sensor 108 is not exposed to large variations in temperature. In many situations, the lower operating temperatures and smaller temperature variations result in an improved oxygen sensor 108 accuracy.

Figure 9:
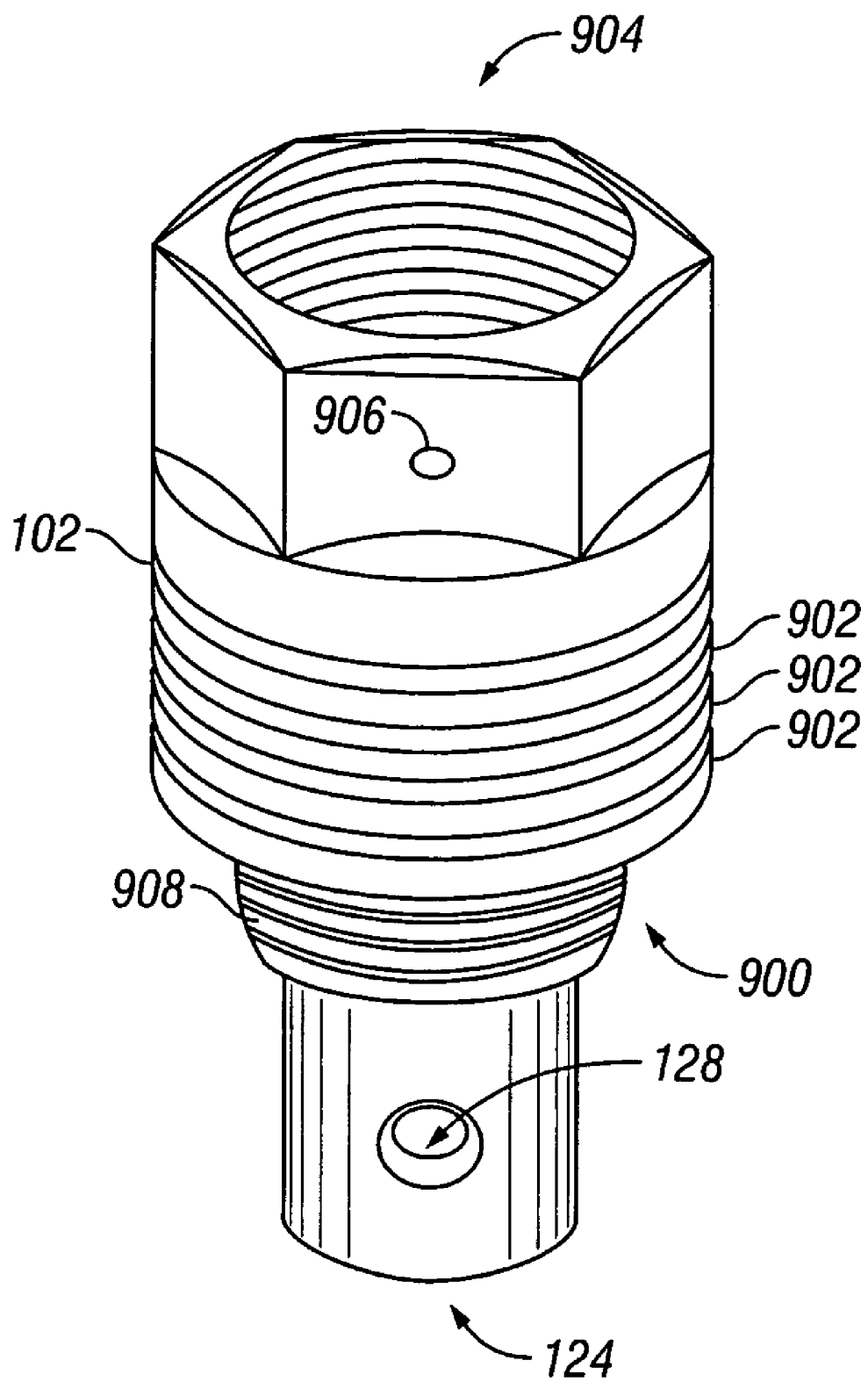
FIG. 9 is an illustration of a perspective view of an exhaust guide in accordance with a fourth exemplary embodiment of the invention.

FIG. 9 is an illustration of a perspective view of an exhaust guide 900 in accordance with a fourth exemplary embodiment. Although any of several materials can be used to form the exemplary exhaust guide 900, the exhaust guide 900 is stainless steel in the fourth exemplary embodiment. The exhaust guide 900 includes threads 908 for screwing the exhaust guide 900 into a bung 502 of an exhaust system. An oxygen sensor 108 is screwed into the threaded opening 904 to position the intake portion 110 of the oxygen sensor 108 within the chamber 112. An alignment marking 906 allows the installer to align the exhaust guide 900 in the preferred orientation within the exhaust system 514. Although the alignment marking 906 may be any type of visual indicator providing information regarding the position of the apertures 124, 128, the alignment marking 906 is a dimple above the input aperture 128. In the fourth exemplary embodiment, the exhaust guide 900 includes several cooling fins 902. The cooling fins 902 are formed by machining radial grooves along the circumference of the body.

Figure 10:
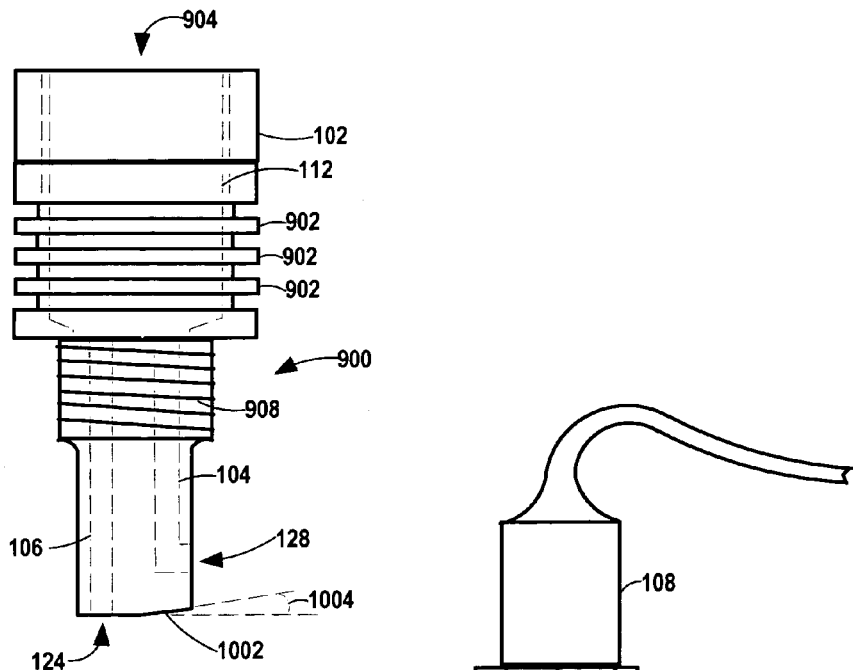
FIG. 10 is an illustration of a side view of the exhaust guide in accordance with the fourth exemplary embodiment of the invention.
Figure 11:
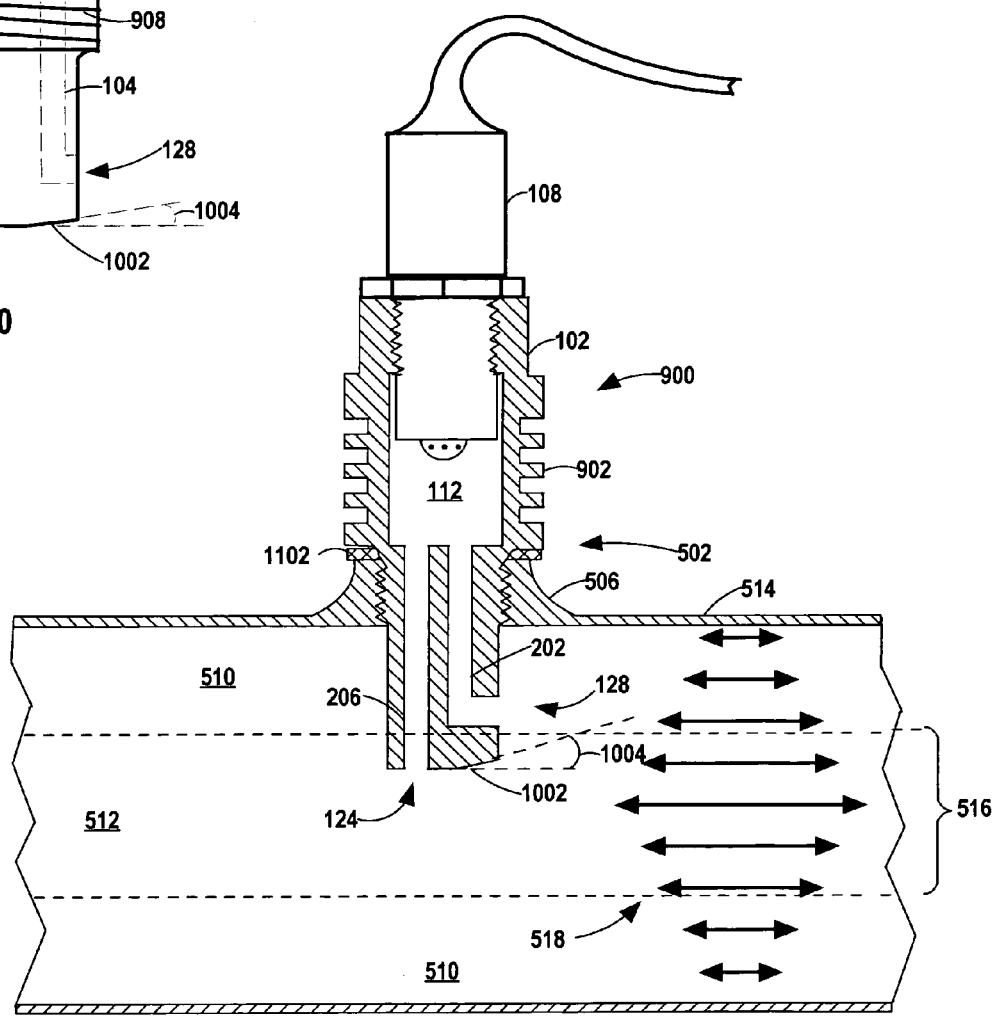
FIG. 11 is an illustration of cross sectional side view of the exhaust guide mounted in an exhaust system in accordance with the fourth exemplary embodiment of the invention.

FIG. 10 is an illustration of a side view and FIG. 11 is a cross sectional side view of the exhaust guide 900 in accordance with the fourth exemplary embodiment. In accordance with known techniques, the exhaust guide 900 is machined from a single piece of stainless steel to form an exhaust guide 900 including at least an input port 104 having an input aperture 128, output port 106 having an output aperture 124 and a chamber housing 102. In the fourth exemplary embodiment, therefore, the input port 104, the output port 106 and the chamber 112 are formed from channels and cavities within a single stainless steel body.

Although the input aperture 128 may have any of several configurations, shapes, and orientations, the input aperture 128 is a circular opening where the plane of the circle defining the opening is perpendicular to the exhaust flow 518 when the exhaust guide 900 is mounted within the exhaust system 514. The angle between the direction of the exhaust flow 518 and the plane of the input aperture is 90 degrees or nearly 90 degrees. The high pressure region 126 is maximized when the plane of the input aperture 128 is perpendicular to the exhaust flow 518.

Although the output aperture 124 may be slightly angled from the direction of the exhaust flow 518 in some circumstances, the output conduit 206 includes a bevel 1002 in the fourth exemplary embodiment. The bevel 1002 has a configuration such that a bevel angle 1004 is formed between the plane of the bevel 1002 and the exhaust flow 518 when the exhaust guide 900 is mounted in the exhaust system 514. Although the angle 1004 may be in the range from 0 to 30 degrees, examples of suitable values of the bevel angle 1004 include values in the range between 1 and 4 degrees. In the fourth exemplary embodiment, the bevel angle 1004 is between 2 and 3 degrees and is approximately 2.5 degrees. Therefore, the bevel angle 1004 may greater than 0, 1, or 2 degrees and/or less than 3, 4, or 30 degrees.

In the fourth exemplary embodiment, the exhaust guide 900 is mounted in the exhaust system 514 by screwing the exhaust guide 900 into a threaded bung 506 that is welded into the exhaust channel 514. The exhaust guide 900 is tightened to crush a compression washer 1102 until the marking 906 is facing the toward the exhaust flow 518. Other mounting mechanisms may be used in come circumstances. A locking washer 508, for example, may be used as described with reference to FIG. 5 in some situations.

The exhaust guide 900 includes a threaded opening 904 to receive the oxygen sensor 108. In the third exemplary embodiment, the oxygen sensor 108 is positioned outside of the exhaust flow 518 when the exhaust guide 900 is secured to exhaust system 514. Positioning the oxygen sensor 108 outside of the exhaust flow 518 reduces the operating temperature of the oxygen sensor 108 in most situations. Since the oxygen sensor 108 is not directly exposed to the hot exhaust gases, the oxygen sensor 108 remains cooler. Further, the oxygen sensor 108 is not exposed to large variations in temperature. In many situations, the lower operating temperatures and smaller temperature variations result in an improved oxygen sensor 108 accuracy.

Accordingly, the exemplary apparatuses, systems, and methods of the present invention facilitate the efficient and accurate measurement of exhaust gases. Exhaust gases are guided through the input port 104, through the chamber 112 that houses the oxygen sensor 108, and out through the output port 106 by creating a high pressure region 126 at the input aperture 128 and a low pressure region 122 at the output aperture 124 when the apertures 124, 128 are positioned with the exhaust flow 114. In the second exemplary embodiment, the oxygen sensor 108 is thermally isolated from the exhaust gases and the exhaust system 116 minimizing the temperature of the oxygen sensor 108.

Those skilled in the art will readily recognize the various modifications and combinations of the embodiments discussed and other alternate embodiments based on the teachings herein. For example, an adapter may be used to provide a mechanism for converting an exhaust guide 200 in accordance with the first exemplary embodiment to an exhaust sensor 500 in accordance with the second exemplary embodiment where additional conduits or channels within the adapter guide the exhaust gases to the input conduit 202 and output conduit 206.

Clearly, other embodiments and modifications of this invention will occur readily to those of ordinary skill in the art in view of these teachings. Therefore, this invention is to be limited only by following claims, which include all such embodiments, equivalents, and modifications when viewed in conjunction with the above specification and accompanying drawings.

What is claimed is:

1. An apparatus for guiding a gas to an intake portion of a sensor, the apparatus comprising:
    a chamber housing having a chamber configured to house at least the intake portion of the sensor;
    an input port connected to the chamber housing; and
    an output port connected to the chamber, the input port and the output port configured to guide the gas from the input port through the chamber to the output port when the input port and the output port are exposed to a gas flow within a gas channel, the apparatus configured for mounting at least a portion of the apparatus within the gas channel to position the output port closer than the input port to a center of the gas channel.

2. An apparatus in accordance with claim 1, wherein the apparatus is configured to create a high pressure region at the input port when the input port is exposed to the gas flow.

3. An apparatus in accordance with claim 1, wherein the apparatus is configured to create a low pressure region at the output port when the output port is exposed to the gas flow.

4. An apparatus in accordance with claim 1, wherein the in put port comprises an input conduit having an input aperture, a plane of the input aperture aligned laterally to the gas flow when the input conduit is positioned within the gas flow.

5. An apparatus in accordance with claim 1, wherein the output port comprises an output conduit having an output aperture, a plane of the output aperture aligned at an angle between one degree and four degrees to the gas flow when the output conduit is positioned within the gas flow.

6. An apparatus in accordance with claim 5, wherein the angle is between two degrees and three degrees.

7. An apparatus in accordance with claim 6, wherein the angle is approximately 2.5 degrees.

8. An apparatus in accordance with claim 1, the apparatus further comprising a mounting mechanism configured to secure the apparatus to a gas channel, the gas flow flowing through the gas channel.

9. An apparatus in accordance with claim 8, wherein at least a portion of the sensor is positioned outside of the gas channel.

10. An apparatus in accordance with claim 8, wherein the mounting mechanism comprises a threaded bung connected to the gas channel.

11. An apparatus in accordance with claim 10, wherein the mounting mechanism comprises a compression washer.

12. An apparatus in accordance with claim 11, further comprising an orientation indicator indicating the orientation of the input port.

13. An exhaust guide for guiding exhaust gases of an engine exhaust gas flow within an exhaust system to an intake portion of an oxygen sensor, the exhaust guide comprising:
   a chamber housing having a chamber configured to house at least the intake portion of the oxygen sensor;
   an input port connected to the chamber housing; and
   an output port connected to the chamber, the input port and the output port configured to guide the exhaust gases from the input port through the chamber to the output port when the input port and the output port are exposed to the engine exhaust flow within a gas channel, the exhaust guide configured for mounting at least a portion of the exhaust guide within the gas channel to position the output port closer than the input port to a center of the gas channel.

14. An exhaust guide in accordance with claim 13, wherein the exhaust guide is configured to create a high pressure region at the input port when the input port is exposed to the exhaust gas flow.

15. An exhaust guide in accordance with claim 13, wherein the exhaust guide is configured to create a low pressure region at the output port when the output port is exposed to the exhaust gas flow.

16. An exhaust guide in accordance with claim 13, wherein the input port comprises an input conduit having an input aperture, a plane of the input aperture aligned laterally to the exhaust gas flow when the input conduit is positioned within the exhaust gas flow.

17. An exhaust guide in accordance with claim 13, wherein output port comprises an output conduit having an output aperture, a plane of the output aperture aligned at an angle between one degree and four degrees to the gas flow when the output conduit is positioned within the exhaust gas flow.

18. An exhaust guide in accordance with claim 17, wherein the angle is between two and three degrees.

19. An exhaust guide in accordance with claim 18, wherein the angle is approximately 2.5 degrees.

20. An exhaust guide in accordance with claim 13, the apparatus further comprising a mounting mechanism configured to secure the exhaust guide to the exhaust system.

21. An exhaust guide in accordance with claim 20, wherein at least a portion of the sensor is positioned outside of the exhaust system.

22. An exhaust guide in accordance with claim 21, wherein the mounting mechanism comprises a threaded bung connected to the exhaust system.

23. An exhaust guide in accordance with claim 22, wherein the mounting mechanism further comprises a compression washer positioned between the threaded bung and a bottom seat of the exhaust guide.

24. An exhaust guide in accordance with claim 20, wherein the mounting mechanism comprises a clamp screw and a clamp arm, the mounting mechanism configured to connect to a tail pipe of the exhaust system.

25. An apparatus for guiding a gas to an intake portion of a sensor, the apparatus comprising:
   a chamber housing having a chamber configured to house at least the intake portion of the sensor;
   an input port connected to the chamber housing; and
   an output port connected to the chamber and comprising an output conduit having an output aperture, a plane of the output aperture aligned at an angle between one degree and four degrees to the gas flow when the output conduit is positioned within a gas flow, the input port and the output port configured to guide the gas from the input port through the chamber to the output port when the input port and the output port are exposed to a gas flow.

* * * * *